US009023417B2

(12) United States Patent
Moulinoux et al.

(10) Patent No.: US 9,023,417 B2
(45) Date of Patent: May 5, 2015

(54) USE OF A POLYAMINE-POOR COMPOSITION FOR THE PRODUCTION OF A MEDICAL HUMAN FOOD

(75) Inventors: Jacques-Philippe Moulinoux, Rennes (FR); Guy Simonnet, Bordeaux (FR)

(73) Assignees: Univeriste de Rennes 1, Rennes Cedex (FR); Universite Victor Segalen Bordeaux 2, Bordeaux Cedex (FR)

( * ) Notice: Subject to any disclaimer, the term of this patent is extended or adjusted under 35 U.S.C. 154(b) by 2429 days.

(21) Appl. No.: 10/566,785

(22) PCT Filed: Jul. 22, 2004

(86) PCT No.: PCT/FR2004/001962
§ 371 (c)(1),
(2), (4) Date: Jan. 12, 2007

(87) PCT Pub. No.: WO2005/020974
PCT Pub. Date: Mar. 10, 2005

(65) Prior Publication Data
US 2007/0184151 A1  Aug. 9, 2007

(30) Foreign Application Priority Data
Jul. 31, 2003  (FR) ..................................... 03 09480

(51) Int. Cl.
| A23L 1/30 | (2006.01) |
| A61K 31/132 | (2006.01) |
| A23L 1/29 | (2006.01) |
| A23L 1/305 | (2006.01) |

(52) U.S. Cl.
CPC ............... *A61K 31/132* (2013.01); *A23L 1/296* (2013.01); *A23L 1/305* (2013.01)

(58) Field of Classification Search
None
See application file for complete search history.

(56) References Cited

U.S. PATENT DOCUMENTS 6,114,392 A    9/2000    Gilad et al. ................... 514/634

FOREIGN PATENT DOCUMENTS

| CA | 2165481 | * 1/1995 | ............. A23L 1/305 |
| EP | 1 085 011 | 9/2000 | |
| WO | WO 95/00041 | 1/1995 | |
| WO | WO 95/00042 | 1/1995 | |
| WO | WO 03/051348 A2 | 6/2003 | |

OTHER PUBLICATIONS

G.M. Gilad et al., "Novel Polyamine Derivatives as Neuroprotective Agents," The Journal of Pharmacology and Experimental Therapeutics, XP-002271148, Oct. 1999, pp. 39-43.
G.M. Gilad et al., "Early Polyamine Treatment Enhances Survival of Sympathetic Neurons after Postnatal Axonal Injury or Immunosympathectomy," Developmental Brain Research, XP-002271146, vol. 38, No. 2, 1988, pp. 175-181.

(Continued)

*Primary Examiner* — Rachael E Bredefeld
*Assistant Examiner* — Dominic Lazaro
(74) *Attorney, Agent, or Firm* — Peter J. Ims; Westman, Champlin & Koehler, P.A.

(57) ABSTRACT

The disclosure relates to a novel use of a food composition for human use, having fewer than 1600 picomoles of polyamines, for the production of a medical food which is intended to combat a syndrome or pathology involving N-methyl-D-aspartate receptor subunit NR2-B.

21 Claims, 4 Drawing Sheets

(56) References Cited

OTHER PUBLICATIONS

G.M. Gilad et al., "Treatment with Polyamines can Prevent Monosodium Glutamate Neurotoxicity in the Rat Retina," Life Science, vol. 44, No. 25, XP-002271147, 1989, pp. 1963-1969.

S. Kergozien et al., "Polyamine Deprivation Provokes an Antalgic Effect," Life Sciences, vol. 58, No. 24, XP-002309789, 1996, pp. 2209-2215.

* cited by examiner

USE OF A POLYAMINE-POOR COMPOSITION FOR THE PRODUCTION OF A MEDICAL HUMAN FOOD

CROSS-REFERENCE TO RELATED APPLICATION

This Application is a Section 371 National Stage Application of International Application No. PCT/FR2004/01962, filed Jul. 22, 2004 and published as WO 2005/020974 on Mar. 10, 2005, not in English.

Field Of The Disclosure

This disclosure relates to the pharmaceutical domain.

More precisely, the disclosure relates to a novel use of polyamine-poor food compositions for the production of a food that may have therapeutic effects.

N-methyl-D-aspartate (NMDA) receptors located at neurone synapses are composed of seven known sub-units, namely NR1, NR2a, NR2b, NR2c, NR2d, NR3a, NR3b.

BACKGROUND OF THE DISCLOSURE

It has been discovered that NMDA receptors, and particularly the NR2B sub-unit, play a critical role in many types of pathologies with a neuron origin. Stimulation of these receptors provokes neurone apoptosis, and consequently induces neuro-degenerative diseases. These receptors are also involved in perception of pain (see J. M. Loftis, A. Janowsky/ Pharmacology & Therapeutics 97 (2003) 55-85).

However, the clinical use of NMDA receptor antagonists is of very limited interest due to the fact that they induce psychotomimetic side effects (hallucinations, mnestic and learning disorders, psychomotor disorders, etc.).

Summary

An embodiment of the invention relates to the new use of a food composition for human consumption containing less than 1600 picomoles of polyamines to make a therapeutic food designed to combat a syndrome or a pathology in which the NR2-B sub-unit of the N-methyl-D-aspartate receptor is involved.

It will be noticed that such food compositions for human consumption are known as such and are described in WO-9500041 issued by the Applicant.

In WO-9500041, these compositions are used as an antineoplastic agent (particularly cancer of the prostate) to stimulate the immunity system, to stimulate the activity of NK cells, to stimulate the endogenic production of interleukine-2 as an antalgic agent and as an agent to reduce the appetite.

Such food compositions may be administered by an enteral method (in other words through the mouth) but also parenteral path, for example using a probe.

In particular, it will be remembered that polyamines and particularly putrescine (I), spermidine (II) and spermine (III) are present in all cells.

 (I)

 (II)

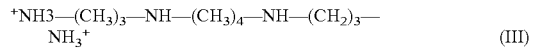 (III)

Although for a long time it has been considered that these molecules do not perform any physiological role and only represent a terminal step in tissular catabolism, a large amount of scientific work has shown that polyamines derived from decarboxylation of ornithine were actually biologically active molecules capable of acting at different important levels in the life of the cell.

These molecules that are found not only inside cells but also circulating in the organism's biological liquids such as blood, are derived from three main sources:
- physiological cell proliferation (growth and/or renewal of cells constituting the organism) and tumoral cell proliferation,
- food
- intestinal bacteria.

Moreover, different work has shown that conjoint administration of:
- polyamine-poor food,
- α-DFMO,
- a polyamine-oxydase (PAO) inhibitor eliminating oxidative retroconversion of spermidine and spermine into putrescine, and
- neomycin and metronidazole, in animals causes a quasi-total inhibition of the tumoral progress of Lewis pulmonary carcinoma 3LL (Seiler N. et al., Cancer Research, 1990, No. 50, pp. 5077-5083), human glioblastome U251 (Moulinoux J-Ph et al., Anticancer Research, 1991, No. 11, pp. 175-180), Dunning MAT-LyLu adenocarcinoma of the prostate (Moulinoux J. Ph. et al., Journal of Urology, 1991, No. 146, pp. 1408-1412) and human neuroblastome neuro 2a (Quemener et al, "Polyamines in the gastro-intestinal tract", Dowling R. H., Folsch I. R. and Loser C Ed., Kluwer Academic Publishers Boston, 1992, pp. 375-385).

It has also been shown in animals that polyamine deprivation can considerably potentialise the antiproliferative effects of conventional antitumoral drugs (methotrexate, cyclophosphamide, vindesine) while extending the survival time of animals and can reduce quantities of administered drugs while maintaining the same antitumoral effect (Quemener V. et al., "Polyamine deprivation enhances antitumoral efficacy of chemotherapy", Anticancer Research No. 12, 1992, pp. 1447-1454).

Therefore, an embodiment of this invention is intended to cover a novel use of such food compositions, which is not obvious from prior art, namely to combat syndromes or pathologies in which the NR2-B sub-unit of the N-methyl-D-aspartate receptor is involved.

In the nervous system, one of the potential effects of polyamides is to act on a membrane site located on the NR1 sub-unit of N-methyl-D-aspartate (NMDA) receptors. By activating this receptor site (polyamine sites), the polyamines would clear the inhibition applied by a site sensitive to protons also located on the NR1 sub-unit (H+sensor proton) itself an inhibitor of the operation of the NMDA receptor channel. Clearing of this inhibition would enable allosteric interactions between sub-units NR1 and NR2B enabling good functioning of the NMDA receptors (Traynelis et al., Science, 1995, 268, 873-876).

The syndromes and pathologies in which the NR2-B sub-unit of the N-methyl-D-aspartate receptor is involved include:
- increased sensitivity and memorisation of pain, and consequently development of chronic pain;
- tolerance to the analgesic effects of opioid analgesics such as morphine and morphinomimetics;
- Alzheimer's disease;
- ischemia;
- Parkinson's disease;
- Huntington's chorea;

epilepsy;
dementia, including dementia following a viral infection;
manic-depressive psychosis and other split personality syndromes;
dependence on different substances with a toxicomanogenic potential (alcohol, tobacco, drugs, etc.) and the resulting compulsive behaviours;
tinnitus.

Therefore this invention could be used to treat these pathologies or syndromes.

Therefore an embodiment of this invention could be used to treat these pathologies or syndromes.

Preferably, the composition used according to an embodiment of this invention contains less than about 400 picomoles/g of putrescine, less than about 400 picomoles/g of spermidine, less than about 400 picomoles/g of spermine and less than about 400 picomoles/g of cadaverine.

Preferably, the composition used according an embodiment of to this invention contains less than about 400 and preferably less than about 200 picomoles/g of polyamines.

Advantageously, the composition used according to an embodiment of this invention contains less than about 100, and preferably less than about 50 picomoles/g of putrescine, less than about 100 and preferably less than about 50 picomoles/g of spermidine, less than about 100 and preferably less than about 50 picomoles/g of spermine, and less than about 100 and preferably less than about 50 picomoles/g of cadaverine. This type of composition provides at least 17 times less putrescine, 40 times less cadaverine, 70 times less spermidine and 220 times less spermine daily than the natural human food with the lowest content of polyamines, but which nevertheless satisfy human nutritional needs.

According to one variant, the composition used according to an embodiment of this invention also includes 10 to 35% by dry weight of lipids, 8 to 30% of proteins, 35 to 80% of glucides, and up to 10% of a mix composed of vitamins, minerals and electrolytes, as a percentage of the total dry weight.

Such a composition may be presented in dry form to be extemporaneously dissolved in a neutral vehicle or in liquid form ready for use. In all cases, the composition is presented in sterile form.

Such a composition is particularly well adapted to man and forms a food substitution that can efficiently create shortages in polyamines taken by patients. Such a composition can feed a patient satisfactorily while inducing a shortage of polyamines, firstly by inhibiting the intracellular synthesis of polyamines, and secondly by reducing the input of exogenic polyamines.

Such a composition can strongly inhibit the endogenic synthesis of polyamines and very significantly reduce the input of these compounds since there is almost none of it in the different ingredients from which it is composed. In order to also reduce polyamine inputs by intestinal bacteria, this composition could be administered concomitantly with decontamination of the gastro-intestinal tract using antibiotic(s) and/or antiparasites(s) for example such as neomycin and metronidazole. It will also be possible to include such antibiotic(s) and/or antiparasite(s) in the said composition directly, without departing from the framework of the invention.

The nutrients used in the food composition according to the invention have good nutritional value even in sick patients.

The quantity of water used to make the composition used according an embodiment of to this invention is determined such that the composition is more or less liquid and can easily be ingested by the patient.

The percentage by weight of the mix composed of vitamins, minerals and electrolytes is chosen so as to satisfy the proportions known to those skilled in the art, required to form a balanced diet.

Preferably, the composition used according to an embodiment of this invention contains less than 100 picomoles/g of putrescine, less than 100 picomoles/g of spermidine, less than 100 picomoles/g of spermine and less than 100 picomoles/g of cadaverine.

Such a composition can be administered jointly to at least one inhibitor of intracellular synthesis of polyamines.

According to one interesting variant of the invention, the composition used according to this an embodiment of the invention is enriched with at least one inhibitor of intracellular synthesis of polyamines, with a content by weight not exceeding 15% of the total dry weight in the composition and preferably between 0.2% and 7% by weight.

In particular, the useable ODC inhibitors are chosen from among the following compounds:
Antagonists of pyridoxal phosphate
L-canaline
N-(5'-phosphopyridoxyl)ornithine Competitive inhibitors
alpha-hydrazino-ornithine
DL-alpha-hydrazino-delta-aminovaleric acid
alpha-methylornithine
trans-3-dehydro-DL-ornithine
1.4-diamino-trans-2-butene
1.4-diaminobutanone
retinol, retinoids, b-carotenes
polyphenols
geraniol
terpenes
flavonoids
procyanidines
resveratrol
Diamine inhibitors
1.3-diaminopropane
1.3-diamino-2-propanol
bis(ethyl)spermine
guanidinobutylamine
Suicide and irreversible inhibitors
2-difluoromethylornithine (DFMO)
monofluoromethylornithine
2-monofluoromethyldehydro-ornithine
2-monofluoromethyldehydro-ornithine methyl ester
5-hexyne-1.4-diamine
trans-hex-2-en-5-yne-1,4-diamine
monofluoromethylputrescine
difluoromethylprutrescine
alpha-allenylputrescine
(2R,5R)-6-heptyne-2,5-diamine.

Competitive inhibitors are particular preferred among these inhibitors, and especially alpha-methylornithine (alpha-MO).

Alpha-methylornithine has many advantages within the framework of the use proposed herein. Alpha-MO has the advantage that it is a natural easily synthesisable compound and has a high inhibition constant.

Alpha-methylornithine also has the advantage of inhibiting the synthesis of polyamines in *Escherischia coli*, the most common bacteria naturally populating the intestinal tract, which in particular is not the case for a-DFMO.

Thus, the use of a food composition according to an embodiment of the invention containing alpha-methylornithine as an inhibitor of the intracellular synthesis of polyamines, can reduce the exogenic input of polyamines by intestinal bacteria without using an antibiotherapy concomitantly with administration of this composition, or at least by reducing the administered dose of antibiotics.

Finally, Alpha-MO has the advantage that it is a simple competitive inhibitor of decarboxylase ornithine and strongly reduces risks of the organism becoming habituated by mutation leading to increased cellular resistance.

According to one variant, use of the composition according to an embodiment of the invention is enriched with vitamins, particularly vitamins added by intestinal bacteria in a healthy human. The antibiotherapy that can accompany administration of the said composition may also reduce the input of some vitamins. In this case, it may be necessary to enrich the composition used in these vitamins in order to avoid provoking a vitamin shortage following prolonged administration of the said composition. In particular, it may be useful to enrich the vitamins or vitamin derivatives in the composition. Some derivatives of vitamin A (retinoic acid) are inhibitors of the ODC activity.

Preferably, glucides in the composition used belong to the group comprising glucose polymers, maltodextrines, saccharose, modified starches, monohydrated glucose, dehydrated glucose syrup, glycerol monostearate and mixes of these products. Such glucides are actually digestible even in the case of a digestive pathology.

According to one variant of the invention, the proteins used belong to the group comprising milk soluble proteins, Soya proteins, serum peptides, powder egg yoke, potassium caseinate, non-phosphorylated peptides, casein peptides, mixed caseinate, soya isolate and mixes of these products.

Preferably, lipids belong to the group including butter oil, peanut oil, medium-chain triglycerides, grape seed oil, soya oil, onagra oil and mixes of these products. Advantageously, the said lipids are composed of a mix of at least one animal oil, at least one vegetable oil and glycerol stearate.

According to one variant of the invention, the composition used according to an embodiment of this invention forms a daily food ration for a human being and includes:
  possibly the said inhibitor of intracellular synthesis of polyamines at a content of less than 50 g and preferably 1 to 10 g,
  between 75 g and 500 g of glucides,
  between 20 g and 185 g of lipids,
  between 20 g and 225 g of proteins,
  sufficient quantities of vitamins, minerals and electrolytes to satisfy the daily nutritional needs of a human being.

Quantities of vitamins, minerals and electrolytes used are known to those skilled in the art and may easily be found in the literature (for example see "Apports nutritionnels conseillés (Recommended nutritional inputs)", Dupin, Abraham and Giachetti second edition 1992, Ed. TEC & DOC Lavoisier).

Such a composition alone can satisfy the daily nutritional needs of a patient while reducing the intracellular synthesis and external input of polyamines. It is also a complete food in itself.

Obviously, such a composition could be administered in several doses taken during the same day rather than all at the same time. Each ration will then be defined by weight so as to form a sub-multiple of a daily food ration for a human being and will include:
  possibly the said inhibitor of intracellular synthesis of polyamines, with a content of less than 50/X g and preferably 1/X to 10/X g,
  between 75/X g and 500/X g of glucides,
  between 20/X g and 185/X g of lipids,
  between 20/X g and 225/X g of proteins,
  sufficient quantities of vitamins, minerals and electrolytes to partially satisfy the daily nutritional needs of a human being.

X is an integer between 2 and 8 corresponding to the number of rations to be ingested by the patient to satisfy his daily nutritional needs.

The number of such rations may be chosen so as to fully satisfy daily food needs of the patient, or may be chosen so as to cover only part of the patient's nutritional needs, the remainder of these needs being provided by natural polyamine-poor food (for example ham and pasta or rice).

In this case, the food composition will be used as a food complement.

The inventors have carried out various operations in order to determine that the application of a polyamine-poor diet for a rat provides a means of combating increased sensitivity and memory of pain, and consequently the development of chronic pain, and also restoring the efficiency of morphine and other substances classified as being morphinomimetic.

DETAILED DESCRIPTION OF ILLUSTRATIVE EMBODIMENTS

Figure 1A:
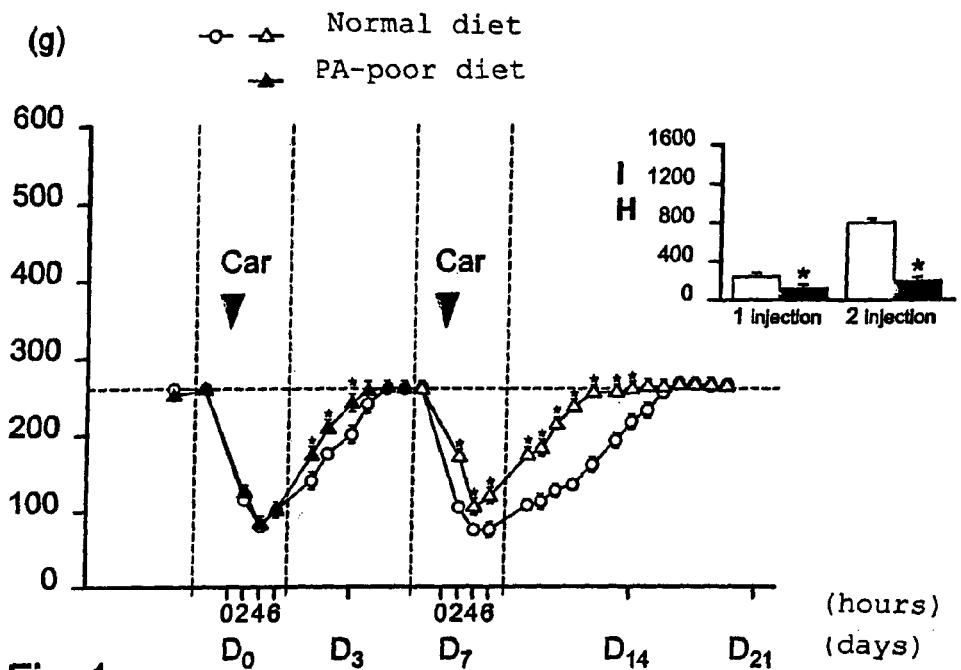
FIGS. 1a, 2a and 2b, 4a and 4b show graphs illustrating the different results of the modified Randal and Sellito test used by the inventors.

Based on possible action mechanisms of polyamines in NMDA receptors, the inventors have determined that by activating polyamine sites of the NR1 fraction, or by modifying the spatial configuration of a loop of 21 amino acids forming this sub-unit (cassette N1) capable of behaving like an analogue of polyamine, the extracellular polyamines played a critical role in the development of phosphorylation of the NR2B sub-unit of NMDA receptors induced by nociceptive influxes. Therefore, they attempted to find if a reduction in exogenic sources of polyamines had a specific impact on the processes to increase sensitivity and memorisation of pain.

To achieve this, Sprague-Dawley rats were fed with a solid food with a very low polyamine content (less than 10 μg of polyamines per kg of food), synthesised as described above (Kergozien et al., Life Sci. 1996, 58, 2209-15) in accordance with the recommendations of Cheauveau et al. (Arch. Sci. Physiol., 1951, 5, 305-322), and satisfying the daily nutritional needs of the rats. This food diet is indicated by "PA-poor diet", on the drawings.

Control animals were fed with the same food plus 54 mg/kg of putrescine, 27 mg/kg of spermidine and 7 mg/kg of spermine at the polyamine concentrations present in standard food for rodents. This food diet is indicated as "normal diet" on the drawings.

At the same time, 2 g/L of neomycin was administered to rats in their drinking water.

In a first step, the effects of a polyamine-poor diet on sensitivity to pain were studied on normal rats using the conventional paw pressure test, and then measuring the rat's scream (modified Randal and Selitto test, Kayser et al., 1990, 508, 329-332).

No change in the nociceptive threshold was observed following a zero polyamine diet for seven days. More precisely, the nociceptive threshold before the polyamine-poor diet was observed at a pressure corresponding to a mass of 280 g on the paw and 281 g after 10 days of a polyamine-poor diet.

Thus, it has been demonstrated that a polyamine-poor diet does not exert an analgesic effect as such.

At the same time, it was observed that this polyamine-poor diet has no influence on the spontaneous nocturnal and diurnal locomotive activity of the tested rats, evaluated according to conventional telemetric records.

At the same time, such a diet also has little effect on rat memory capacities as evaluated by conventional space recognition tests.

No change in body temperature nor weight was observed in the rats tested.

Thus, unlike antagonists of NMDA receptors, polyamine-poor diets given for several days do not introduce any noticeable psychotomimetic side effects in the rat.

In a second step, the inventors studied the consequences of a polyamine-poor diet in the process of development of sensitivity to pain, by comparing the effects of two successive injections (0.2 ml) of a saline solution with 1% of carrageenan (CAR) into the paws of animals. The sensitivity to pain was evaluated using the Randall Selitto test and the degree of pain was evaluated by an original test (Postural Unbalance test) that quantitatively evaluated changes to postural pressures on the rat's rear paws using a strain gauge system (Rivat et al., 2002, World Congress on Pain Abstract, 10, 381-382). The advantage of this test lies in the fact that due to a quantitative evaluation of an antalgic behaviour (postural unbalance on the rear paws), it can be used to evaluate a spontaneous pain level not requiring the use of brief and discontinuous experimental nociceptive stimuli as in the case of most conventional tests that only evaluate sensitivity to pain (nociceptive threshold). A second advantage of this test is that it can quantitatively evaluate the real efficiency of a supposed antalgic treatment in the same way as for man in a clinic.

Figure 1B:
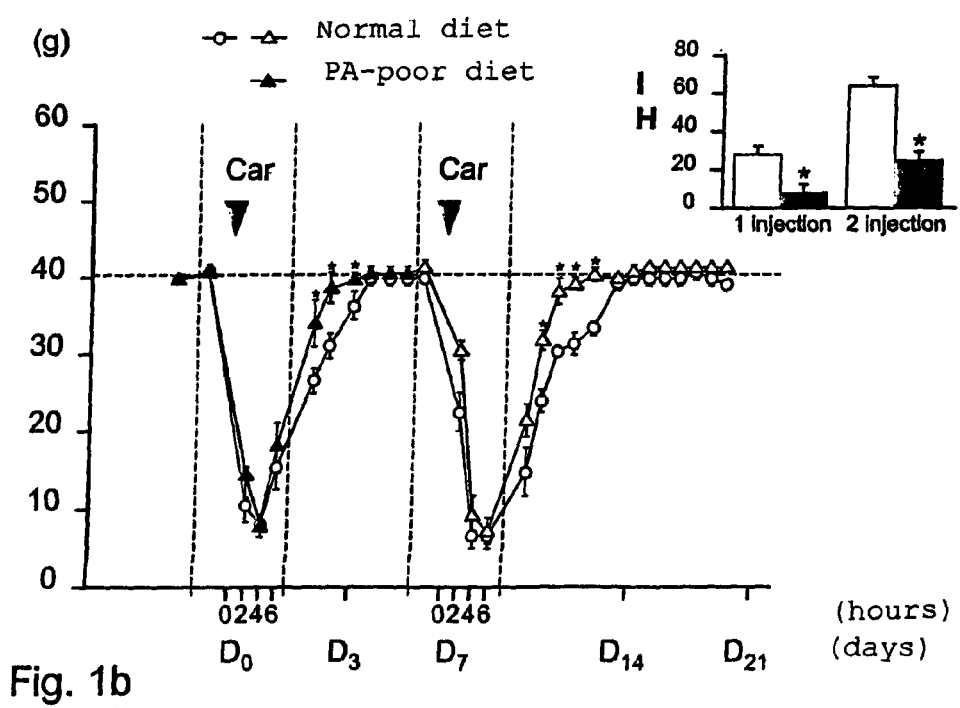
FIGS. 1b, 2c and 2d, 4c and 4d show graphs illustrating the results of the "postural unbalance" test used by the inventors.
Figure 2A:
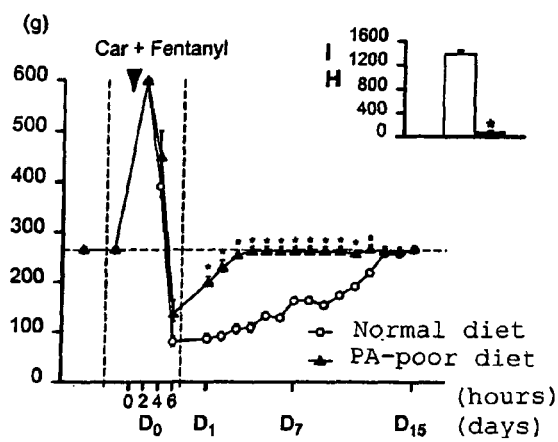
Figure 2B:
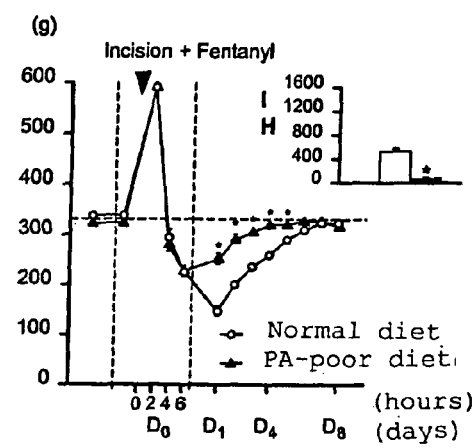
Figure 2C:
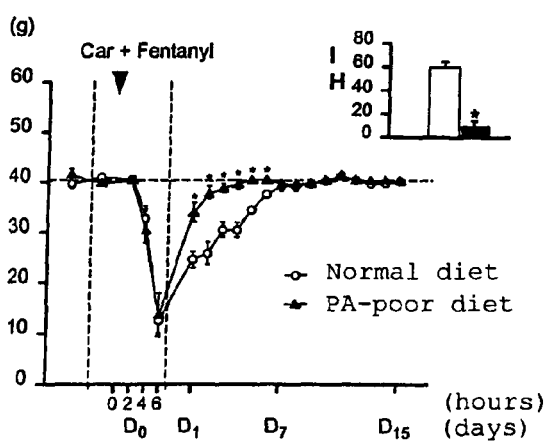
Figure 2D:
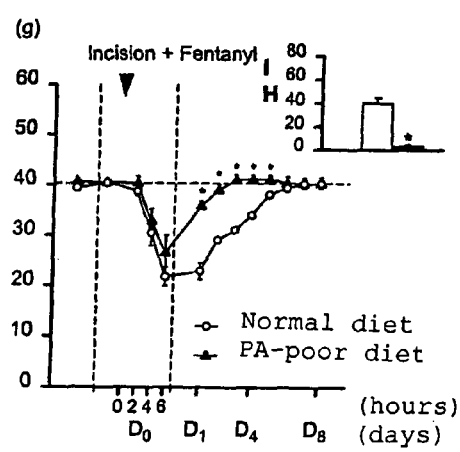

As shown in FIG. 1a and FIG. 1b, there is no effect on the nociceptive threshold or on the pain level recorded during the first injection of carrageenan (DO in rats that had received a polyamine-poor diet for seven days before inflammation). However, when the polyamine-poor diet has been given for seven or more days, the hypersensitivity to pain and the increase in the degree of pain observed during subsequent days were significantly lower than what was observed with rats fed normally.

Thus, in rats for which the polyamine-poor diet was stopped the day before a second injection of carrageenan (FIG. 1a-"D7"), the increase in hyperalgesia (sensitivity to pain) following a second inflammatory stimulus was completely eliminated in rats who had previously been subjected to a polyamine-poor diet. Therefore the polyamine-poor diet prevents hyperalgesia associated with the first and with the second injection of the carrageenan.

This proves that a polyamine-poor diet that is completely free of an anti-inflammatory effect opposes development of the sensitivity to pain resulting regularly from successive inflammatory nociceptive stimuli, and therefore slows memorisation.

In a third step, the effect of a polyamine-poor diet was tested in rats on an incisional pain model of the surgical type, incised according to Brennan et al. Is model (Pain 1996, 64, 493-501) and treated by an opioid widely used in human clinical treatment (fentanyl).

As can be seen in FIGS. 2a to 2d, the polyamine-poor diet completely eliminates the increased long term hyperalgia due to fentanyl, induced by both inflammatory pain and by incisional pain. This preventive effect is also observed in terms of sensitivity to pain (Randall-Selitto test, FIG. 2a-b) and in terms of the pain level (Postural Unbalance Test, FIGS. 2c-d).

In a fourth step (see FIGS. 4a to 4d), the tests were carried out on rats suffering from sustainably established mono-arthritic pain provoked by the injection of a Freund additive (CFA) (Butler et al. Pain, 1992, 48, 73-81) or pain with a neuropathic source by ligature of the sciatic nerve (Bennet and Xie, Pain, 1988, 33, 87-107). The efficiency of small doses of morphine was also evaluated in these animal models, knowing that although neuropathic pain is not completely resistant to morphine, it is recognised as being not very sensitive to morphine or its derivatives.

These tests show that the sensitivity to pain (Nociceptive threshold, Randall-Selitto test) and the sensation of pain (Postural Unbalance Test) were significantly reduced within a few days in rats receiving a polyamine-poor diet. Furthermore, the polyamine-poor diet improved the efficiency of small doses of morphine, particularly in rats with neuropathic pain.

It might be thought that, due to the use of polyamine-poor compositions according to an embodiment of the invention, it will be possible to restore the analgesic effect of opioid substances such as morphine in man.

Figure 3:
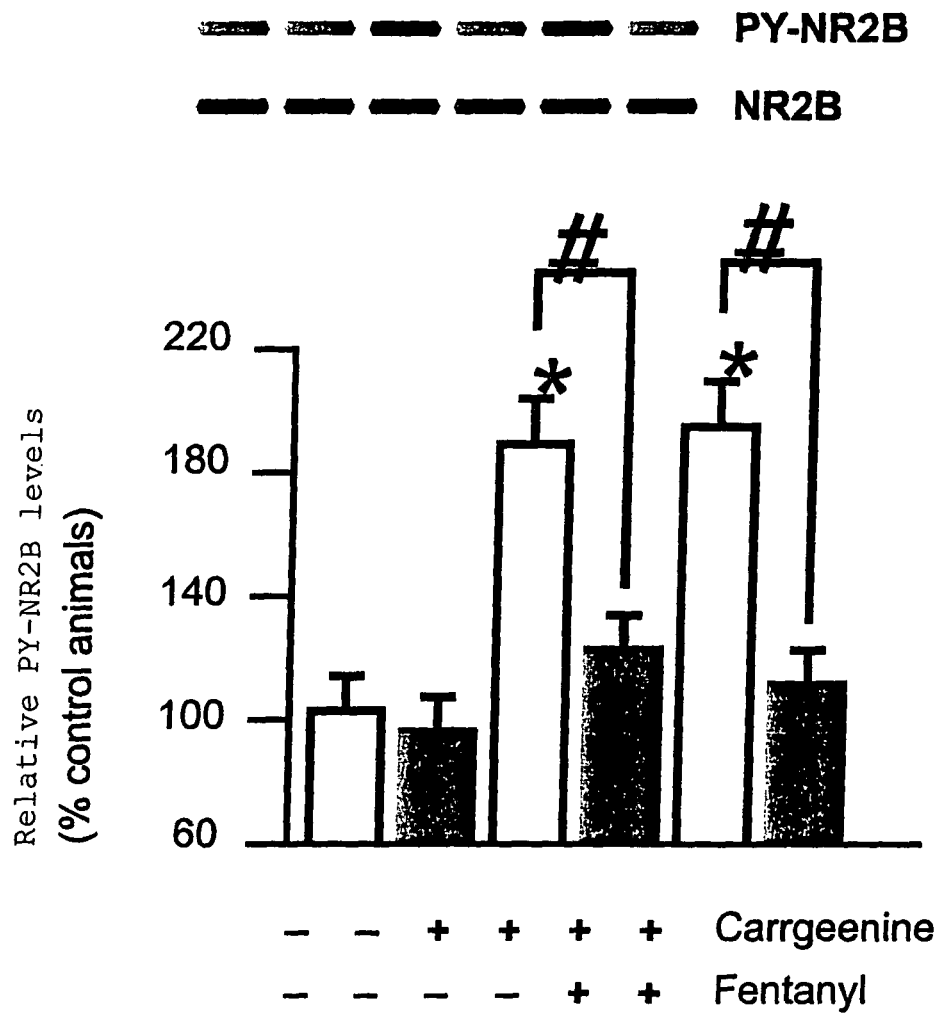
FIG. 3 shows an electrophoretic gel and a graph illustrating the influence of consumption of a polyamine-poor diet on the phosphorylation level of the tyrosine residue of the NR2B sub-unit of the NMDA receptor.
Figure 4A:
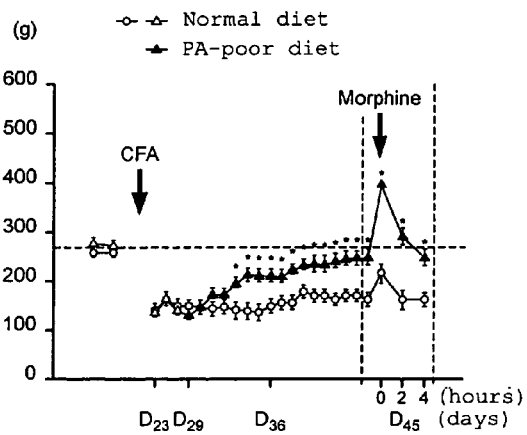
Figure 4B:
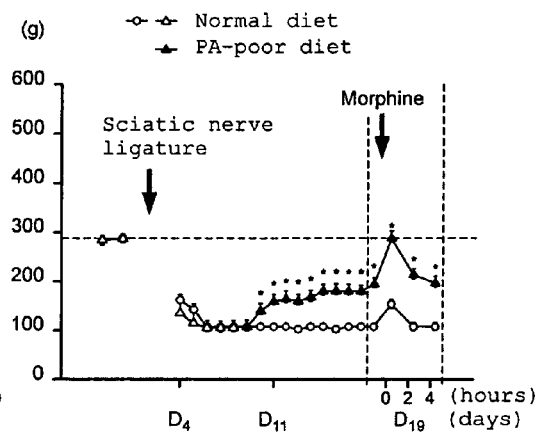
Figure 4C:
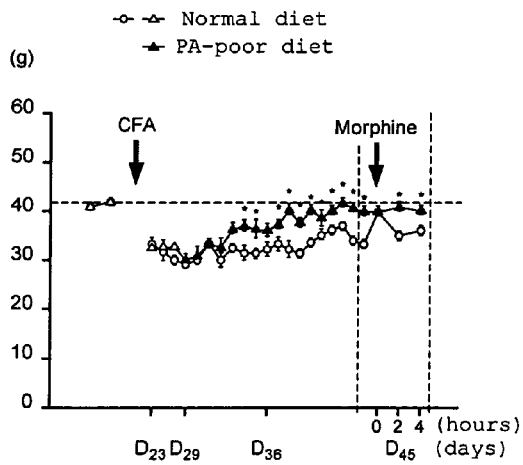
Figure 4D:
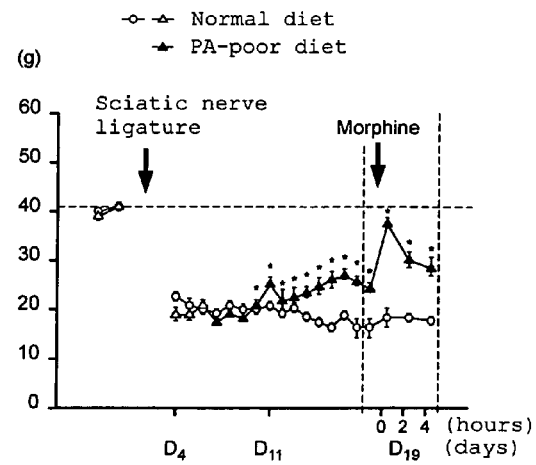

With reference to FIG. 3, proteins from the spinal cord (region L4-L5) were extracted from the lower spine in animals that were or were not subjected to an inflammatory stimulus, that were or were not fed with a polyamine-poor diet, and were or were not treated by fentanyl. Spots located in the upper part of the electrophoresis (1) reveal proteic bands corresponding to proteins extracted by immunoprecipitation in the presence of anti-NR2B antibodies, and then revealed in the presence of PY-99 anti-phosphotyrosine antibodies. The spots located in the lower part (2) show the immunoreactivity of extracted proteins as in (1), this time revealed by anti-NR2B antibodies, but these proteins had previously reacted with antiphosphotyrosine antibodies PY-99. The histograms express the intensity of phosphorylation of the tyrosine residue of the NR2B sub-unit of the NMDA receptor (1) compared with (2), during the different treatments. The plain text columns correspond to control animals fed with food containing polyamines (as described above); the black columns correspond to animals that have been fed with a polyamine-poor diet. The results are expressed in average ±SEM (*) $p<0.05$.

Thus, the polyamine-poor diet has completely eliminated the increase in phosphorylation of the NR2B sub-unit of NMDA receptors induced by inflammatory type pain provoked by injection of carrageenan, in the spine.

By reducing the hypersensitivity to pain component related to phosphorylation of the NR2B sub-unit of NMDA receptors, and without eliminating the pain itself, polyamine-poor compositions according to an embodiment of the invention can be used in the context of non-invasive nutritional therapies capable of improving control over different types of painful syndromes in the long term.

An embodiment of this invention proposes an alternative to the use of such antagonists to efficiently inhibit functioning of the NR2B sub-unit of NMDA receptors, in other words without inducing any major undesirable effect.

Thus, an embodiment of this invention proposes a therapeutic agent that could be used to treat neuro-degenerative diseases induced by stimulation of this sub-unit.

Another purpose of an embodiment of this invention is to propose a therapeutic agent capable of blocking the development of increased sensitivity to pain, memorisation of pain and consequently the development of chronic pain.

In particular, an embodiment proposes a therapeutic agent capable of restoring the analgesic effects of opioid substances by opposing the tolerance process.

Opioids such as morphine are powerful and widely used analgesics. However, they also cause dose-dependent development of hypersensitivity to pain in the long term (so-called pronociceptive effect) that can cause long-term hyperalgesia. (exaggerated painful sensation to a nociceptive stimulus) and allodynies (painful sensation to a non-nociceptive stimulus). This increase in sensitivity to pain may be caused by the development of tolerance to analgesic effects (Simonnet et al., NeuroReport, 2003, 14, 1-7).

Although the present invention has been described with reference to preferred embodiments, workers skilled in the art will recognize that changes may be made in form and detail without departing from the spirit and scope of the invention.

The invention claimed is:

1. A method for treating a syndrome or a pathology having increased sensitivity and memorization of pain, and consequently development of chronic pain, the treatment comprising:
    administering a food composition to a human where the human is exhibiting long-term, increased pain sensitivity to a nociceptive stimulus; wherein the food composition comprises a daily food ration containing less than 1600 picomoles of polyamines, and wherein the pathology of an NR2-B subunit of an NMDA receptor is affected after administration, resulting in prevention of the development of chronic pain in the human.

2. The method according to claim 1, wherein said composition contains less than 400 picomoles/g of putrescine, less than 400 picomoles/g of spermidine, less than 400 picomoles/g of spermine and less than 400 picomoles/g of cadaverine.

3. The method according to claim 1, wherein said composition contains less than 200 picomoles/g of polyamines.

4. The method according to claim 1 wherein said composition contains less than 50 picomoles/g of putrescine, less than 50 picomoles/g of spermidine, less than about 50 picomoles/g of spermine, and less than 50 picomoles/g of cadaverine.

5. The method according to claim 1, wherein said composition includes 10 to 35% by dry weight of lipids, 8 to 30% of proteins, 35 to 80% of glucides, and up to 10% of a mix composed of vitamins, minerals and electrolytes, as a percentage of the total dry weight.

6. The method according to claim 5, wherein said composition is enriched with at least one inhibitor of intracellular synthesis of polyamines, with a content by weight not exceeding 15% of the total dry weight of the composition.

7. The method according to claim 6, wherein said composition is enriched with the said inhibitor with a content by weight of between 0.2% and 7% of the total dry weight of the composition.

8. The method according to claim 7, wherein said inhibitor is a competitive inhibitor of decarboxylase ornithine.

9. The method according to claim 8, wherein said competitive inhibitor of the said composition is alpha-methylornithine.

10. The method according to claim 1, wherein said composition contains at least one antibiotic.

11. The method according to claim 1, wherein said composition is enriched with vitamins.

12. The method according to claim 5, wherein said glucides in the composition are selected from the group consisting of: glucose polymers, maltodextrines, saccharose, modified starches, monohydrated glucose, dehydrated glucose syrup, glycerol monostearate and mixes of these products.

13. The method according to claim 5, wherein said proteins in the composition are selected from the group consisting of: milk soluble proteins, Soya proteins, serum peptides, powder egg yoke, potassium caseinate, non-phosphorylated peptides, casein peptides, mixed caseinate, soya isolate and mixes of these products.

14. The method according to claim 5, wherein said lipids in the composition are selected from the group consisting of: butter oil, peanut oil, medium-chain triglycerides, grape seed oil, soya oil, onagra oil and mixes of these products.

15. The method according to claim 5, wherein said lipids in the composition are selected from the group consisting of: at least one animal oil, at least one vegetable oil, and glycerol stearate and mixtures of these products.

16. The method according to claim 1, wherein said composition forms a daily food ration for a human being and includes:
    between 75 g and 500 g of glucides,
    between 20 g and 185 g of lipids,
    between 20 g and 225 g of proteins, and
    vitamins, minerals and electrolytes.

17. The method according to claim 1, wherein said composition forms a daily food ration for a human being and includes:
    less than 50 g of at least one inhibitor of intracellular synthesis of polyamines,
    between 75 g and 500 g of glucides,
    between 20 g and 185 g of lipids,
    between 20 g and 225 g of proteins, and
    vitamins, minerals and electrolytes.

18. The method according to claim 1, wherein said composition is a sub-multiple of a daily food ration for a human being and in that it includes:
    between 75/X g and 500/X g of glucides,
    between 20/X g and 185/X g of lipids,
    between 20/X g and 225/X g of proteins,
    vitamins, minerals and electrolytes, and
    X is an integer between 2 and 8 corresponding to the number of rations to be ingested by the human to satisfy the human's daily nutritional needs.

19. The method according to claim 1, wherein said composition is a sub-multiple of a daily food ration for a human being and in that it includes:
    less than 50/X g of at least one inhibitor of intracellular synthesis of polyamines,
    between 75/X g and 500/X g of glucides,
    between 20/X g and 185/X g of lipids,
    between 20/X g and 225/X g of proteins,
    vitamins, minerals and electrolytes, and
    X is an integer between 2 and 8 corresponding to the number of rations to be ingested by the human to satisfy the human's daily nutritional needs.

20. The method according to claim 1, wherein said composition is presented in dry form to be extemporaneously dissolved in a neutral vehicle.

21. The method according to claim 1, wherein said composition includes a neutral vehicle making it ready for use.

* * * * *